(12) United States Patent
Vanden Bussche et al.

(10) Patent No.: US 6,713,036 B1
(45) Date of Patent: Mar. 30, 2004

(54) PROCESS FOR MIXING AND REACTING TWO OR MORE FLUIDS

(75) Inventors: Kurt M. Vanden Bussche, Lake in the Hills, IL (US); Suheil F. Abdo, Lincolnshire, IL (US); Anil R. Oroskar, Oakbrook, IL (US)

(73) Assignee: UOP LLC, Des Plaines, IL (US)

( * ) Notice: Subject to any disclaimer, the term of this patent is extended or adjusted under 35 U.S.C. 154(b) by 353 days.

(21) Appl. No.: 09/850,438

(22) Filed: May 7, 2001

(51) Int. Cl.$^7$ ............... C01B 15/01; C07D 201/04; C07D 301/03; C07D 301/12; C07D 309/00
(52) U.S. Cl. ............... 423/584; 423/659; 540/535; 564/253; 549/273; 549/295; 549/523; 549/531; 252/373
(58) Field of Search ............... 423/584, 659; 549/273, 295, 531, 523; 540/535; 564/253

(56) References Cited

U.S. PATENT DOCUMENTS

| | | | | | |
|---|---|---|---|---|---|
| 3,361,533 A | * | 1/1968 | Hooper | ............... | 423/584 |
| 4,007,256 A | * | 2/1977 | Kim et al. | ............... | 423/584 |
| 4,146,359 A | * | 3/1979 | Lumpkin et al. | ............... | 432/14 |
| 4,832,938 A | * | 5/1989 | Gosser et al. | ............... | 423/584 |
| 5,194,242 A | * | 3/1993 | Paoli | ............... | 423/584 |
| 5,266,291 A | * | 11/1993 | Drnevich et al. | ............... | 423/376 |
| 5,360,603 A | * | 11/1994 | Drnevich et al. | ............... | 423/584 |
| 5,641,467 A | * | 6/1997 | Huckins | ............... | 423/584 |
| 6,042,804 A | * | 3/2000 | Huckins | ............... | 423/584 |
| 6,117,409 A | * | 9/2000 | Bertsch-Frank et al. | ............... | 423/584 |
| 6,210,651 B1 | * | 4/2001 | Nystrom et al. | ............... | 423/584 |
| 6,299,852 B1 | * | 10/2001 | Nystrom et al. | ............... | 423/584 |
| 6,447,743 B1 | * | 9/2002 | Devic et al. | ............... | 423/584 |
| 6,471,937 B1 | * | 10/2002 | Anderson et al. | ............... | 423/659 |

OTHER PUBLICATIONS

*Microreactors, New Technology for Modern Chemistry*, by W. Ehrfedl, V. Hessel, H. Löwe, Wiley–VCH 2000, pp. 41–85 (No Month).

Microreaction technology: industrial prospects; proceedings of the Third International Conference on Microreaction Technology/IMRET2 by T.M. Floyd et al., W. Ehrfeld, Springer 2000, pp. 171–179 no month.

* cited by examiner

*Primary Examiner*—Wayne A. Langel
(74) *Attorney, Agent, or Firm*—John G. Tolomei; Frank S. Molinaro; Arthur E. Gooding

(57) ABSTRACT

A novel process for continuously mixing and reacting at least two fluids are disclosed. Excellent mixing and superior pressure drop characteristics are achieved using cyclone mixing where at least two supply channels feed a mixing chamber to create a vortex of the fluids to be mixed. The alignment of the supply channels is such that fluids are introduced into the chamber at both tangential and radial directions. In the case of gas/liquid mixing, particularly advantageous is the injection of the liquid stream tangentially and the gas stream radially. Reaction of the fluids can take place within the mixing chamber or in a separate reactor in fluid communication with the mixing chamber outlet. The process is especially useful for reacting potentially explosive mixtures of reactants where a homogeneous reactor feed mixture is critical to maintaining a non-explosive environment.

16 Claims, 2 Drawing Sheets

$H_2O_2$ PRODUCTION AT CONSTANT $H_2$ FLOW

PROCESS FOR MIXING AND REACTING TWO OR MORE FLUIDS

FIELD OF THE INVENTION

The present invention relates to a novel process for mixing and reacting at least two fluids. The process comprises supplying at least two fluids into a mixing chamber through conduits leading thereto in both tangential and radial directions. The well-mixed fluid stream may be reacted either in the mixing chamber itself or downstream in a separate reactor. Applicable processes include those where highly efficient mixing is critical, for example in the direct production of hydrogen peroxide from hydrogen and oxygen.

BACKGROUND OF THE INVENTION

When mixing at least two fluids, the objective is to achieve a uniform distribution as rapidly as possible. It is advantageous to use the static mixers described by W. Ehrfeld, V. Hessel, H. Löwe in *Microreactors, New Technology for Modern Chemistry,* Wiley-VCH 2000, p. 41–85. Known static mixers achieve mixing times for liquids between several milliseconds and 1 second by generating alternate adjacent fluid layers of micrometer range thickness. The higher diffusion constants for gases provide even more rapid mixing. In contrast to dynamic mixers, where turbulent flow conditions prevail, the predetermined geometry of static mixers allows precise fixing of the fluid layer widths and diffusion paths. As a result, a very close distribution of mixing times is achieved. This allows numerous possibilities for optimizing chemical reactions with regard to selectivity, yield, and even safety.

A further advantage of static mixers is a reduction in component size, allowing greater ease of integration with adjoining equipment, such as heat exchangers and reactors. Process optimization may also be enhanced due to forced interactions between two or more components within a confined space. Static mixers apply to forming not only liquid/liquid and gas/gas mixtures, but also liquid/liquid emulsions and liquid/gas dispersions. Static mixers have also found use in multiphase and phase-transfer reactions.

A static mixer operating using the principle of multilamination or fluid layering has, in one plane, a structure of intermingled channels of a width of about 25–40 microns (i.d., pp. 64–73). The channels divide two fluids to be mixed into a multiplicity of separate fluid streams, arranged to flow parallel and alternately in opposite directions. Adjacent fluid streams are removed vertically upward out of a horizontal plane and through a slot and are brought into contact with one another. Using structuring methods suitable for mass production, however, the channel geometries and therefore the fluid layer widths can be reduced to the submicron range to only a limited extent.

A further reduction in the size of fluid layers using the multilamination principle is achieved by so-called geometric focusing. A static mixer using this principle for reacting hazardous substances is described by T. M. Floyd et al. in *Microreaction technology: industrial prospects; proceedings of the Third International Conference on Microreaction Technology/IMRET3,* W. Ehrfeld, Springer 2000, pp. 171–179. Alternately adjacent channels for the two fluids to be mixed open outward in a semicircle, radially from the outside, into a chamber extending into a funnel shape and merging into a narrow, elongate channel. The layered fluid stream is combined in the chamber and then transferred to the narrow channel, so that the individual fluid layer width is reduced. Under these laminar flow conditions, mixing is purely diffusional. Therefore, mixing times in the millisecond range are achieved by reducing the fluid layer width to the submicron range. A drawback with this configuration is that the narrow channel must be sufficiently long to achieve full, intimate mixing. This requires a large structure and promotes relatively high pressure loss.

In contrast to these disclosures, the present invention provides a solution to the well-known problem of mixing at least two fluids rapidly and uniformly, while at the same time maintaining low pressure drop characteristics and an economical design. The efficient mixing provided is especially useful in combination with chemical reactions where extremely good dispersion of reactants can overcome diffusion limitations and/or even reduce hazards where an explosive mixture of feed components is involved. In terms of the latter benefit, the present invention can be integrated with many types of oxidation reactions or those involving selective combustion to provide internal heating. Oxidation reactions to which the present invention applies include, for example, the direct oxidation of ethylene to ethylene oxide, as described in U.S. Pat. No. 4,212,772. Another reaction of particular interest is in the manufacture of hydrogen peroxide from hydrogen and oxygen, described in U.S. Pat. No. 4,832,938.

Currently the most widely practiced industrial scale production method of hydrogen peroxide is an autooxidation process employing alkylanthraquinone as the working material. This process comprises dissolving alkylanthraquinone in an organic working solution to perform reduction, oxidation, separation by aqueous extraction, refining, and concentration operations. Overall, the use of a solvent phase adds complexity and requires high installation and operating costs.

Considerably more simple and economical than the alkylanthraquinone route is the direct synthesis of hydrogen peroxide from gaseous hydrogen and oxygen feed streams. However, this approach carries the serious risk of explosion of the gaseous mixture of feed components in stiochiometric quantities. It is well known that oxygen-hydrogen gaseous mixtures have one of the greatest potentials for explosion. That is, explosive concentrations of hydrogen in an oxygen-hydrogen gaseous mixture at normal temperature and pressure are from 4.7% to 93.9% by volume. Thus the range is extremely broad. It is also known that dilution of the gaseous mixture with an inert gas like nitrogen scarcely changes the lower limit concentrations of the two gases. Within normal ranges of pressure variation (1–200 atmospheres) and temperature variation (0–100° C.) the explosive range is known to undergo little change.

In contrast to the prior art, the present invention uses highly effective mixing of a potentially explosive mixture of reactants to overcome the inherent safety considerations. Essentially, the rapid and complete mixing allows the reactants to be chemically transformed without any significant amounts of unreacted components being present in explosive concentrations for any significant length of time. The present invention is therefore suitable for a number of oxidative and combustive reactions. Prior to reaction, the feed components are mixed in a manner utilizing a vortex or mixing chamber that promotes complete mixing without significant pressure loss. Although the invention may be used in a wide variety of applications, the invention is particularly suited for small-scale or micromixing operations that are coupled with reaction.

In the specific case where the present combined mixing/reaction process is used in the preparation of hydrogen peroxide through the direct reaction of hydrogen and oxygen, a considerable cost savings is realized over the above mentioned alkylanthraquinone route. A cheaper method of hydrogen peroxide production also favorably impacts the economics of downstream uses, such as in the further reaction of hydrogen peroxide with propylene to form propylene oxide.

SUMMARY OF THE INVENTION

The present invention is a method of rapidly and continuously mixing and thereafter reacting at least two fluids. The method overcomes limitations of high pressure drop and insufficient diffusion. Mixing is accomplished by injecting streams of individual fluids in both tangential and radial directions about a mixing chamber to provide an overall helical flow path. Although the invention may be used in a wide variety of applications, the invention is particularly suited for small-scale mixing operations, or micromixing.

In one embodiment, the present invention is a process for continuously mixing and reacting components that have a potential to exist within their flammability envelope. The process comprises mixing a feed stream and an oxidant with a characteristic mixing time to yield a mixed reactant stream. The process further comprises reacting the feed stream and the oxidant, with a characteristic reaction time, in a reaction zone at effective reaction conditions and in the presence of a catalyst to yield an oxidized product, where the ratio of the characteristic mixing time to the characteristic reaction time is less than about 1.

In another embodiment, the present invention is a process as described above where the feed stream comprises hydrogen, the oxidant comprises oxygen, and the product stream comprises hydrogen peroxide. The hydrogen and oxygen may or may not be mixed in a ratio within their flammability envelope.

In yet another embodiment, the present invention is a process for continuously mixing and reacting at least two fluid streams. The process comprises flowing a first fluid stream through a first feed channel and injecting the first fluid stream in a substantially radial direction into a mixing chamber. The process further comprises flowing a second fluid stream through a second feed channel and injecting the second fluid stream in a substantially tangential direction into the mixing chamber to create a vortex. The process further comprises reacting the first and second fluids within the mixing chamber at reaction conditions and in the presence of a catalyst to yield a product stream, and also comprises withdrawing the product stream from the central portion of the vortex.

In another embodiment, the present invention is a process for reacting at least two fluid streams. The process comprises flowing a first fluid stream through a first feed channel and injecting the first fluid stream in a substantially radial direction into a mixing chamber. The process further comprises flowing a second fluid stream through a second feed channel and injecting the second fluid stream in a substantially tangential direction into the mixing chamber to create a vortex. The process further comprises withdrawing a stream of mixed first and second fluids from the central portion of the vortex and reacting the stream of mixed fluids in a reaction zone at reaction conditions and in the presence of a catalyst to yield a product stream.

These and other embodiments and objects will become clearer after the detailed description of the invention.

DETAILED DESCRIPTION OF THE INVENTION

Figure 1:
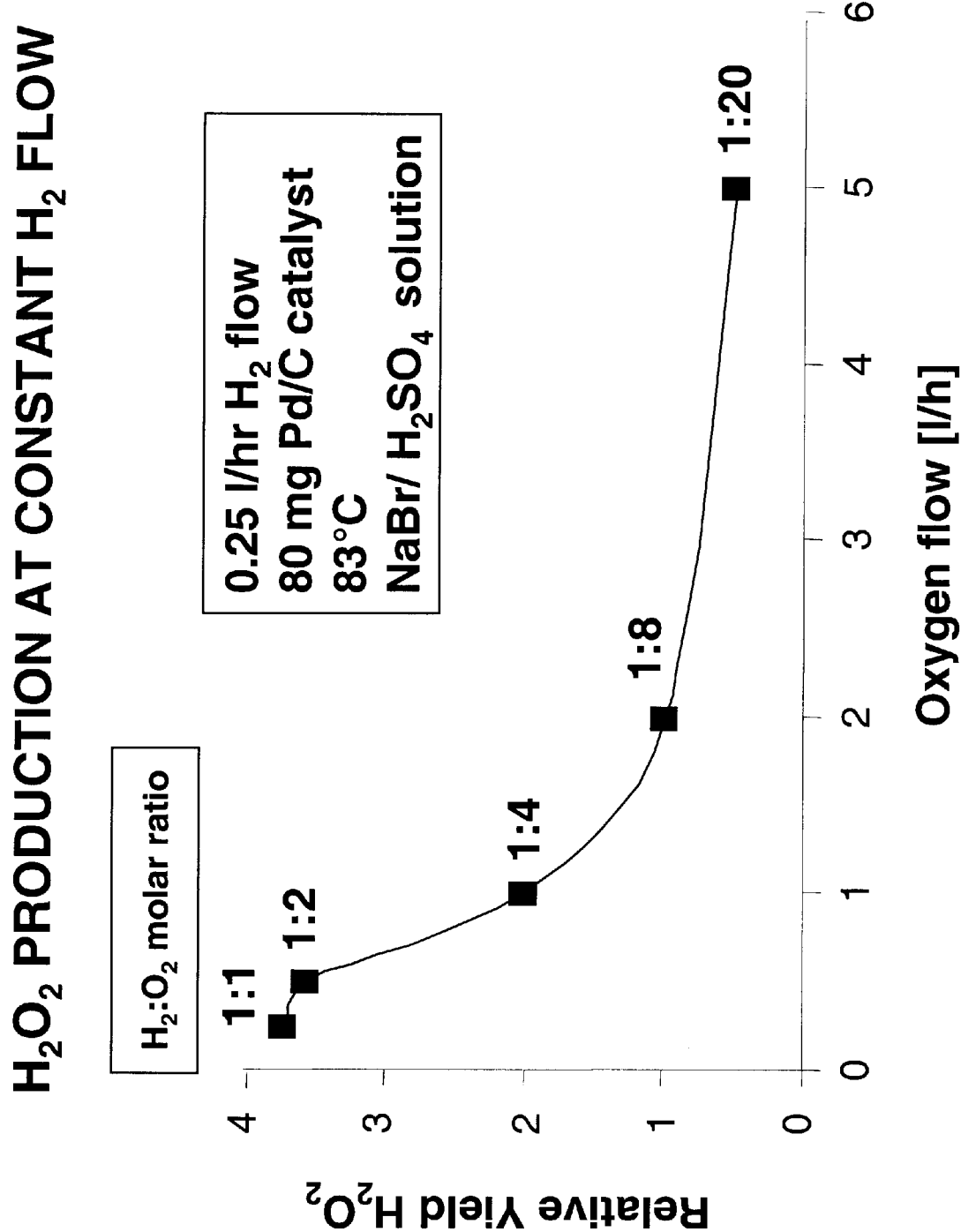
FIG. 1 shows the relationship between hydrogen peroxide product yield and the hydrogen:oxygen molar ratio at a constant flow of hydrogen through the reactor.

As mentioned, the invention relates to an improved method for continuously mixing and reacting two or more fluids. The fluids can be broadly any gaseous or liquid substances or mixtures of substances. The fluids may also have solid components dissolved or dispersed therein, so that solutions of dissolved solids and slurries, for example slurries of liquid reactants containing solid catalyst particles, are also applicable to the present invention. Other fluids comprising multiple phases such as gas/liquid mixtures, particle-entrained gases, and three-phase slurries are also pertinent. The mixing achieved prior to reaction, according to the present invention, also encompasses the known operations of dissolving, emulsifying, and dispersing. Consequently, the resulting mixture includes solutions, liquid/liquid emulsions, and gas/liquid and solid/liquid dispersions. The mixing/reaction process according to the invention is advantageously applied in forming a gas/liquid dispersion, in which case at least one fluid introduced into a mixing chamber contains a gas or a gas mixture and at least one further fluid introduced contains a liquid, a liquid mixture, a solution, a dispersion, or an emulsion.

The mixing/reaction process according to the present invention is used for carrying out chemical reactions, especially those characterized as diffusion limited. Also of particular interest are reactions involving reactant mixtures that can exist at explosive concentrations, or within their flammability envelope. In some cases, it is desired to mix, prior to reaction, isolated streams containing individual reactants, such that the homogeneous mixture of these individual reactants would fall outside of the flammability envelope. In this situation, rapid mixing prior to reaction is desired to bring the reaction mixture to homogeneity quickly, eliminating the existence of localized concentrations in explosive proportions. While the possibility for explosion exists when conventional mixing is employed, it can be essentially eliminated when the mixing time that is required to reach substantial homogeneity is less than the reaction time required to reach substantial conversion. Therefore, it is preferable that the mixing operation of the present invention be characterized in that the ratio of the characteristic mixing time to the characteristic reaction time be less than about 1. The characteristic mixing time, $t_{mix}$, as described by Ehrfeld, V. Hessel, H. Löwe, *Microreactors, New Technology for Modeni Chemistry*, Wiley-VCH 2000 at page 41 is given by:

$$T_{mix} \sim d_1^2/D,$$

where $d_1$ is the fluid layer or lamella width and D is the diffusion coefficient of the components to be mixed. This quantity represents the time required, from the completely isolated component state, to reach a percentage of homogeneity about 63% [i.e. one time constant is $(1-e^{-1}) \cdot 100\%$]. Thus, the smaller the fluid layer boundary width, the smaller the characteristic mixing time. Similarly the characteristic reaction time, $t_{rx}$, represents the time required, from the initial state of unconverted reactants, to a product representing about 63% of the equilibrium conversion. In a first order reaction, $t_{rx}$ is the reciprocal of the reaction rate constant.

Therefore, mixing operations that achieve preferably a ratio of $t_{mix}/t_{rx}$ of less than 1 are useful for overcoming diffusion problems or explosion hazards. According to the above explanation, these mixing operations, as they pertain to fast chemical reactions, will often require very small boundary layer thicknesses of the individual fluid streams to be mixed. These small layer dimensions may be achieved using specialized micromixers, capable of generating thin layers on the nanometer scale, such as those described by W. Ehrfeld et al. using microfabrication techniques also explained therein. Other devices that can provide such ultrafast mixing capability are described later.

As mentioned, in static mixing, the mixing time is primarily a function of the distance between boundary layers of adjacent reactant fluids that are injected into the mixing chamber. Considering the example of mixing pure hydrogen and oxygen and then reacting these components to form hydrogen peroxide, maintaining the feeds in proportions outside of their respective flammability envelope will eliminate the explosion hazard. However, the transition from pure components to the non-explosive homogeneous condition will necessary involve the fluid boundary layers "passing through" the flammability envelope for a finite time. Any transient or localized concentration gradients therefore present an explosion risk even when, in the totally homogeneous condition, the reactants are non-explosive. For these reasons, the direct mixing of hydrogen and oxygen has until now not been considered a commercially viable route to hydrogen peroxide. The present invention comprising both mixing and reaction operations is associated with the realization that the extremely rapid attainment of substantial homogeneity will preclude the possibility of explosion that would otherwise exist.

In other cases, where even the homogeneous mixture of reactants, such as the 1:1 molar mixture of hydrogen and oxygen, is within the flammability envelope, the use of proper dimensions associated with the reaction zone and transfer conduits thereto can prevent explosion hazards. Without being bound to any particular theories, two mechanisms, free radical formation and insufficient heat dissipation, are typically used to explain explosivity. Free radical formation and propagation as a description for runaway of the reaction system was described by Semenov and more recently by Maas and Warnatz. Walls of channels wherein explosions may occur are considered "third bodies" that quench the reaction by neutralizing the radicals. As such, the surface to volume ratio of the reaction vessel is crucial in determining combustion/explosivity. The second theory, pioneered by Fraul-Kamenetsky, compares the heat release to the heat removal potential. Since heat release is proportional to reaction volume and heat removal is directly proportional to the wall surface area, a similar criterion as that announced by Mass and Warnatz is derived.

Therefore, in order to prevent the explosion of gaseous mixtures in proportions within the flammability envelope, the use of small equipment directionally provides a greater surrounding surface area for the adsorption of either free radicals or heat generated. Specifically, it has been determined that using a conduit of less than about 200 $\mu$m in diameter leading to the reaction zone significantly reduces the possibility for explosion upstream of the reactor.

Reactions that involve mixing potentially explosive reactant combinations include oxidations. Specific oxidation reactions for which the mixing/reaction process of the present invention is suited include, but are not limited to, the direct synthesis of hydrogen peroxide from hydrogen and oxygen, as described in U.S. Pat. No. 4,832,938 and the production of ethylene oxide from ethylene and oxygen, as described in U.S. Pat. No. 4,212,772. Partial oxidation reactions are also relevant to this process. In the production of synthesis gas, those skilled in the art routinely balance the endothermic heat requirements of the primary reforming with the partial oxidation of hydrocarbons to provide a secondary reforming reaction. The operation of an adiabatic reformer for synthesis gas production is shown and described in U.S. Pat. No. 4,985,231. Additionally, the process of the present invention also applies to combustive heating of reaction mixtures, as applied, for example, in U.S. Pat. No. 4,599,471 where oxygen is introduced in a dehydrogenation reactor to maintain isothermal conditions as well as shift the reaction equilibrium toward the desired $C_3^+$ olefin product formation. While the above processes may use pure oxygen as a reactant, they may also use air for convenience. Broadly, therefore, feed streams applicable to the present invention include hydrogen, hydrocarbons, and mixtures thereof.

In the case of hydrogen peroxide manufacture, hydrogen and oxygen are most advantageously mixed, from purely a chemistry standpoint and with a view toward minimizing recycle, in equimolar or stoichiometric proportions, meaning that the reactants are each present in a concentration of 50% by volume. Because this mixture lies well within the flammability envelope, it did not represent a practical mode of operation prior to the present invention, which provides a highly efficient means of mixing the reactants upstream prior to reaction. Using a small-scale mixing or micromixing according to the present invention, hydrogen and oxygen may be combined in an explosive ratio due to the relatively large surface areas of surrounding walls. Applicants have determined that these surfaces are integral to mitigating the potential for explosion, due to their ability to absorb free radicals and/or energy and heat formed at the outset of the explosion. Specifically, when a conduit is used to pass a well-mixed reactant stream from the mixing chamber to a downstream reaction zone, it is preferable that this conduit have a diameter of less than about 200 $\mu$m. The use of a sufficiently narrow conduit for transferring the reaction mixture has allowed operation, without explosion, over the entire range of flammability for hydrogen and oxygen mixtures. These mixtures are characterized in that molar ratio of hydrogen to oxygen is from about 0.05 to about 15.

As mentioned, in one embodiment the process of the present invention comprises direct mixing of hydrogen and oxygen to form hydrogen peroxide, where the reactants are mixed prior to reaction in a non-explosive ratio, or outside of the flammability envelope. When this mode of operation is used, it is preferable that hydrogen and oxygen are mixed continuously in a proportion of about 3% hydrogen by volume and about 97% oxygen by volume. While hydrogen/oxygen mixtures generally having less than about 4.7% hydrogen by volume are non-explosive, the establishment of this mixture from pure components always includes a transient period where at least some of the reactants are within the flammability envelope and pose an explosion hazard. Therefore, the rapid mixing achieved using the present invention is important to its utility for reacting potentially explosive mixtures.

While the present invention, in the specific case of hydrogen peroxide production, may be used to react pure hydrogen and oxygen streams, it is also possible to react any hydrogen and oxygen containing streams available in a convenient, impure form. For example, hydrogen feed stream may comprise hydrogen diluted with other light gases such as methane. An oxygen feed stream may be introduced as an air stream. However, impurities introduced with the gaseous feed components may prove uneconomical when downstream purification measures are considered.

Also, these impurities do not significantly impact the region of flammability of the mixture, which depends primarily, although not solely, on the ratio of explosive components. This ratio is not significantly affected by dilution.

Effective conditions appropriate for the production of hydrogen peroxide from hydrogen and oxygen are known in the art and include a temperature from about 20° C. to about 90° C., an absolute pressure from about 1 to about 100 atmospheres, and a gas hourly space velocity from about 50 to about 50,000 hr$^{-1}$. As is understood in the art, the gas hourly space velocity is the volumetric hourly feed rate of gaseous components to the reactor divided by the reactor volume. Preferably, the hydrogen peroxide production reaction occurs in the presence of a solid catalyst. Specifically, catalysts comprising a noble metal (e.g. platinum or palladium) deposited on a solid support have been found especially useful. Preferable support materials include inorganic refractory metal oxides (e.g. alumina), carbon, and polymers (e.g. polytetraflouroethylene).

The catalytic reaction zone or reactor may be located within the mixing chamber into which reactant streams are introduced. Otherwise, the reactants may first be mixed in a separate mixing chamber prior to being introduced into a reaction zone through a conduit used for the transfer of these reactants. In the first case, solid catalyst may be contained within the mixing chamber or catalyst may be disposed therein by coating the mixing chamber inner and/or bottom surfaces with catalytic metal using known methods such as deposition from solution or vapor. If the reaction zone is maintained separate, it is appropriate to feed reactants thereto through the mixing chamber outlet. Furthermore, it may be desirable to recycle unconverted reactants exiting the reactor back to either the mixing chamber or the inlet of the reactor.

The hydrogen peroxide generated according to the present invention may be further reacted to form other industrially useful products, such as propylene oxide. For example, the $H_2O_2$ direct synthesis from hydrogen and oxygen may be conveniently integrated with a process for the production of olefins and co-production of hydrogen, to yield oxidized products. Examples of olefin-generating processes are known in the art and include, for example, the dehydrogenation of $C_2$–$C_{14}$ paraffins to olefins and hydrogen, as described in U.S. Pat. No. 4,886,928. The conversion of methanol to light olefins and hydrogen using aluminosilicates or zeolites as catalysts described in, for example, U.S. Pat. Nos. 4,238,631, 4,328,384, and 4,423,274. The thermal cracking of hydrocarbons to yield unsaturated components (e.g. ethylene) and hydrogen is described, for example, in U.S. Pat. No. 4,215,231. Since these processes are capable of producing olefins, it is possible to react the hydrogen peroxide produced in the present invention with any of the effluent streams described above containing $C_2$–$C_5$ olefins, such as a paraffin dehydrogenation process effluent, a methanol-to-olefins process effluent, a thermal cracking process effluent, and mixtures thereof to yield a $C_2$–$C_5$ oxide product. (e.g. propylene oxide). Particularly attractive with this integration between processes is the ability to use the co-produced hydrogen effluent streams from any of the above processes as a feedstock for the $H_2O_2$ production process.

Other commercially significant end products result from downstream reactions with hydrogen peroxide. For example, oxidized aromatic compounds such as phenol are produced by reacting hydrogen peroxide with benzene, as described in U.S. Pat. No. 5,233,097. Epoxides such as propylene oxide are formed by the reaction of olefins (e.g. alkenes and cycloalkenes) and hydrogen peroxide in the presence of a titanosilicate catalyst, as described in U.S. Pat. No. 5,354,875. Lactones such as caprolactone are produced from the catalyzed oxidation of ketones with hydrogen peroxide in the presence of a carboxylic acid or an anhydride, as described in U.S. Pat. No. 5,665,891. Finally, oximes such as cyclohexanone oxime, a precursor to caprolactam, is formed by the ammoximation of carbonyls (e.g. cyclohexanone) with hydrogen peroxide and ammonia, as described in U.S. Pat. No. 5,227,525.

As described in detail below, the reactant streams may be introduced separately into a mixing chamber or they may be pre-mixed in supply conduits leading to this chamber. The optimal choice depends on the specific nature of the reaction. For example, reactions requiring long residence times may be best effected using pre-mixing, while reactions where explosive mixtures may result locally due to non-uniform mixing are best carried out by avoiding contact between reactants upstream of the mixing chamber. Known methods of controlling the chemical reaction, such as, for example, the use of temperature or pressure sensors, flow meters, heater elements, or heat exchangers, can be integrated with the mixing/reaction process. Where the mixing/reaction is carried out using an assembly of sealingly connected layers comprising one or more plates, these control devices may be arranged at a layer above or below the mixing chamber and may be functionally connected thereto. As mentioned, to carry out heterogeneously catalyzed chemical reactions, the mixing chamber may additionally contain catalytic material.

Depending on the specific chemical reaction for which intimate mixing of the reactants is desired, it may be advantageous for various other fluids to be introduced into the mixing chamber. Such supplemental fluids include, for example, chemical stabilizers, emulsifiers, corrosion inhibitors, reaction promoters, polymerization chain terminating agents, and the like. Even a solid or liquid catalyst may be introduced into the mixing chamber to carry out the desired reaction. Of course, the reactant fluids to be mixed may already contain an admixed auxiliary substance. The mixture formed in the mixing chamber, whether or not the reaction also takes place in the mixing chamber by disposing catalyst therein, is removed via a mixing chamber outlet in fluid communication with the mixing chamber, preferably at its central region.

The present invention relies on efficient mixing of reactants to overcome potential explosion hazards and/or diffusion limitations. In cases where the homogeneous reaction mixture is outside the flammability envelope, rapid mixing is essential to establishing this non-explosive condition prior to reaction. In other cases where the reaction mixture lies within the flammability envelope, a combination of efficient mixing and a proper reactor inlet conduit dimension is essential. Types of mixers and mixing processes that can achieve these characteristics are described in the aforementioned references by W. Ehrfeld, V. Hessel, H. Löwe in *Microreactors, New Technology for Modern Chemistry,* Wiley-VCH 2000, p. 41–85 and also by T. M. Floyd et al. in *Microreaction technology: industrial prospects; proceedings of the Third International Conference on Microreaction Technology/IMRET*3, W. Ehrfeld, Springer 2000, pp. 171–179. These multilaminar mixing processes, with or without geometric focusing, provide the necessary degree of efficiency and may be fabricated to micron-scale dimensions. In addition to these types of mixing processes, cyclone mixing, which incorporates a mixing chamber to create a vortex of reactant streams to be mixed, is novel and also appropriate. The major characteristic of any type of mixing process that is applicable to the mixing/reaction process of the present invention is, as explained earlier, that the characteristic mixing time is less than the characteristic reaction time.

Using cyclone mixing, the mixing/reaction process according to the present invention for mixing at least two fluids prior to reaction comprises flowing reactant streams to a mixing chamber through at least two feed channels used for injecting the fluids into the chamber and arranged about the perimeter of the mixing chamber. The particular fluids are introduced at defined flow rates and trajectories into the mixing chamber so that they form a fluid spiral flowing concentrically inward. This vortex formation extends the fluid residence time within the mixing chamber considerably, thereby improving mixing characteristics. Establishment of the desired helical and inward liquid flow path is primarily a function of both the angle of fluid introduction into the mixing chamber and the fluid kinetic energy. Fluids introduced radially, or, in the case of a cylindrical mixing chamber, directly toward its center, will not assume a helical flow path unless acted upon by another fluid with sufficient kinetic energy in the tangential direction. The present invention achieves exceptional mixing by introducing the first and second fluids to be mixed both tangentially and radially. It is preferred that the tangential fluid kinetic energy components are adequate to bend the radial flow components so that they assume the overall helical flow pattern with a sufficient number of windings to allow effective mixing. Since one fluid is introduced tangentially and another radially, it is preferred that the ratio of fluid kinetic energy of the tangentially flowing fluid to that of the radially flowing is greater than about 0.5 to provide the desired helical and inward flow pattern.

When proper conditions are established to form the desired helical flow pattern, only that fluid flowing along the outermost winding of the helix contacts the lateral inner surface of the mixing chamber. Depending on the shape and dimensions of the mixing chamber, this fluid accounts for a significant fraction of the pressure drop in the mixing chamber due to frictional losses. Fluid comprising the inner windings, in contrast, is in contact on both sides with rotating fluid only. This fluid comprises previous and subsequent windings flowing in the same direction. For these reasons, the pressure loss achieved with the mixing/reaction process of the present invention is lower than that possible for processes employing a static mixer using multilamination only and with a correspondingly long mixing path. In the multilamination case, the fluids flow as alternating layers in opposite directions. Therefore, frictional effects between adjacent fluid streams flowing along straight or curved pathways are larger. The advantages associated with using the cyclone mixing in the present invention for mixing fluids prior to reaction may therefore be realized in terms of a low pressure loss as well as both a large contact area and long residence time available for diffusive mixing within a small structure, prior to reaction. While a compact design in the form of a micromixer, having catalyst contained therein, may be conveniently fabricated, the present invention does not exclude operation at intermediate or even larger scales.

A further advantage of the particular case where cyclone mixing is used with the present invention is that one winding of the fluid spiral or vortex contacts both the previous and subsequent windings, contributing to the diffusive mixing of the reactants. Preferably, laminar flow conditions prevail from the circular fluid motion in the interior of the mixing chamber. However, it is also possible for localized turbulent flow conditions to result from the overall inward flow of the fluid spiral or vortex.

To form an inward helical flow path, at least one of the reactant fluids is directed so that it opens at an acute angle or tangentially into the mixing chamber. Furthermore, the fluids may be introduced either as their bulk composition prior to mixing, or as fluid boundary layers that have been pre-mixed to some extent before entering the mixing chamber. Generally, the tangentially directed fluid maintains laminar flow conditions upon entry into the mixing chamber, in order to form the desired fluid vortex with a multiplicity of windings extending perpendicularly with respect to the plane of the vortex.

The fluids to be mixed may open out in one plane around the common mixing chamber. Without regard to the number of supply conduits used to introduce fluids, a minimum of two being required, the supply conduits are preferably distributed symmetrically around the circumference of the mixing chamber. These supply conduits can be used to supply the same reactant fluids, for example the reactant A may be supplied separately in each of supply conduits 1 and 3, while reactant B is supplied in conduits 2 and 4. Otherwise, each conduit can supply a different fluid, for example conduits 1, 2, 3, and 4 can supply the fluids A, B, C, and D, respectively. Furthermore, the supply channels can be arranged in a plurality of planes around the mixing chamber. The same or different fluids can be introduced into the mixing chamber at supply channels arranged in any given plane. Therefore, fluids may be introduced into a common type of mixing chamber, for example one having a circular cross section in a horizontal plane, through supply channels at various axial heights about the mixing chamber. Such a design could achieve an even longer fluid spiral, corresponding to longer residence times within the mixing chamber.

The mixing chamber is preferably substantially cylindrical in shape and therefore preferably has a substantially circular cross section. It is also possible that the cross section is circular but that the circle diameter decreases or increases with axial height, so that the mixing chamber is actually conical rather than cylindrical in shape. The mixing chamber cross section is advantageously fixed in a substantially horizontal plane from which the mixing chamber outlet leads substantially perpendicularly or in a general vertical direction. Of course, the mixing chamber may have another cross sectional shape, particularly a rounded form such an oval or ellipse. Even triangular or other polygonal forms may be acceptable. However, corners formed at the vertices of such shapes, if not rounded to some extent, may promote "dead" zones (i.e. regions without a constant flow) that could be reduce mixing effectiveness. In the preferred case of a cylindrically shaped mixing chamber, the height of the supply conduits, at least in the region where they open into the mixing chamber, is preferably less than or equal to the height of the mixing chamber.

In a preferred embodiment, multiple supply channels alternately open tangentially and radially into the mixing chamber. This particular case is especially useful for providing gas/liquid dispersions that are to be reacted. Here, supply channels for the liquid streams optimally open into the mixing chamber at a more acute angle than those for the gas streams. As a result, the gas streams are broken into individual gas bubbles by the swirling liquids. Particularly preferably, supply channels for the liquids open tangentially into the mixing chamber, and the supply channels for the gases open radially into the mixing chamber. This arrangement promotes the formation of gas/liquid dispersions with a small, closely distributed bubble size and thus provides an essentially homogeneous mixture prior to reaction.

The mixing/reaction process further comprises supplying a stream of mixed fluids for downstream applications through a mixing chamber outlet. The mixing chamber outlet is in fluid communication with, and withdraws mixed fluid from, the central region of the mixing chamber, preferably at its center point. For example, if the mixing chamber is cylindrical and therefore has a circular cross section, the mixing chamber outlet will extract mixed fluid from its center. In a preferred embodiment, the mixing chamber has a substantially circular cross section oriented horizontally and the mixing chamber outlet leads substantially perpendicularly, either upward or downward, therefrom. The cross-sectional area of the outlet compared to that of both the mixing chamber and the cross-sectional areas of the supply channels opening into it will be set, in view of the specific fluids and their properties, to allow the formation of the desired inwardly flowing fluid vortex with a multiplicity of windings. Preferably, the mixing chamber outlet conduit has a circular cross section, as would be the case for a pipe or tube, and the ratio of the diameters of the mixing chamber and mixing chamber outlet is greater than about 5.

In the case where catalyst used to carry out the reaction of the well-mixed reactants is not disposed within the mixing chamber or introduced as a fluid stream, a separate reactor is required downstream of the mixing chamber. In this case, the reactor will then normally contain a catalyst within a catalyst retention space. It is also possible that the catalyst is introduced continuously, for example, as a solid dispersed in a liquid reactant slurry, into the reactor.

If it is further desired to separate the reaction product exiting the reactor, it is also possible to incorporate a separator downstream of the reactor. The separator in this case will have an inlet for the reaction product, as well as at least two outlets for each of an overhead and a bottoms stream. Depending on the relative volatility and/or other properties of the reactant feeds, reaction products, and byproducts, it may also be desired to recycle either the bottoms or overhead product back to the mixing chamber. The recycle stream may be introduced into the mixing chamber either through a tangentially or radially directed supply conduit. Otherwise, it is also possible to pre-mix the recycle stream with one of the reactant streams, in a manner described below, prior to introducing the recycle stream to the mixing chamber. Another possibility is to recycle the separated fluid, or a portion thereof, to the mixing chamber outlet directly upstream of the catalyst bed. Of course, the separator may use any number of known separation techniques known in the art, including flash separation, distillation, membrane separation, extraction, crystallization, and the like.

In another embodiment, one or more additional fluids enter into the mixing chamber either through a separate supply conduit or through a supply conduit where the additional fluid is pre-mixed with one of the fluids to be mixed. Such additional fluids may contain an auxiliary substance that stabilizes the mixture, for example an emulsifier. If further supply channels are used to supply such a substance, they advantageously open tangentially into the mixing chamber, so that there is in each case one stream of the additional fluid between adjacent windings of the fluid spiral. Otherwise, if further supply channels are used to supply a gaseous component into a fluid vortex which contains at least one liquid in the mixing chamber, these supply channels for the gas advantageously open into the mixing chamber radially or at an intermediate angle between tangentially and radially. As a result, the gas that is supplied is broken up into small gas bubbles by the fluid spiral and is finely dispersed.

As mentioned previously, surprisingly good mixing characteristics are obtained when at least one of the supply conduits provides a substantially tangential injection of fluid into the mixing chamber and at least one also provides a substantially radial injection. It is the tangential fluid motion that imparts a spiral or vortex formation within the chamber, which breaks apart or finely divides the radially flowing fluid. By radial flow is meant a fluid flow directed toward the center of the mixing chamber, whether the chamber be circular, elliptical, or oval in shape. Tangential flow refers to a flow directed at a right angle to this radial flow and generally at or near the surface of the mixing chamber. Substantially tangential or radial flow means that the superior mixing characteristics of the present invention may also be obtained when the flows are not exactly tangentially or radially directed, but are within about 30° of these directions.

In a preferred embodiment, the mixing/reaction process comprises using not merely two, but a plurality of supply conduits leading alternately substantially tangentially and substantially radially to supply fluids into the mixing chamber. The term "alternately" refers to the tangentially directed supply conduits, designated T, and the radially directed supply conduits, designated R, lying in the order TRTR in at least one plane about the mixing chamber. The supply channels may also lie alternately in more than one plane, for example they may be offset in the manner of a chess board in two dimensions about the circumference and length of the mixing chamber. By varying the positions, in both the horizontal and vertical planes, from which fluids are introduced into the mixing chamber, multiple helical flow paths may be formed, flowing concentrically inward. Thus, for example, a type of double or even triple spiral may be effected. These fluid spirals lie together in one plane and around one center, in such a manner that the respective windings lie adjacent to one another.

Furthermore, not only are the supply conduits arranged in alternating tangential and radial directions about the mixing chamber, but they are also preferably in alternating fluid communication with respect to the first and second fluids to be mixed. In the case of mixing a gas stream with a liquid stream, which may be desired, for example, to effect a chemical reaction, exceptional results in terms of mixing have been achieved where the gas and liquid streams are injected radially and tangentially, respectively, into the mixing chamber. Without adherence to any particular mechanism or theory, it is believed that the tangentially directed liquid breaks the radially flowing gas stream into fine bubbles upon entry into the mixing chamber. As mentioned previously, it is preferable that the kinetic energy of the tangentially introduced fluid is at least 0.5 times that of the radially introduced fluid. This ensures the overall formation of an inwardly flowing spiral or vortex to provide a sufficient residence time for effective mixing. In the specific case mentioned previously where hydrogen and oxygen streams are the fluids introduced into the mixing chamber to be mixed prior to reaction to form hydrogen peroxide, it is preferred that the oxygen stream is introduced tangentially, as this component generally has a significantly greater kinetic energy than the hydrogen stream.

It is important to note that it is not necessary for entire supply conduits to be oriented in these directions, only those terminal portions in proximate fluid communication with the mixing chamber and impacting the fluid direction into the chamber. For this reason, it is appropriate to refer to the supply conduits as having respective receiving and discharge ends. The receiving ends are in fluid communication with the fluids to be mixed, or feeds, and the discharge ends are in fluid communication with the mixing chamber and are responsible for directing the fluid flow with respect thereto. One possibility is that the supply channels may be of substantially uniform cross section over their entire length from their receiving end to their discharge end. A substantial change in direction from the receiving end to the discharge end of a supply conduit is certainly possible and may even be desired if space about the mixing chamber for multiple conduits is limited. Otherwise, acceleration of the fluid into the mixing chamber, which is often desired to improve mixing, is conveniently accomplished through the narrowing of a supply conduit in the direction from its receiving end to its discharge end. Particular supply conduits that narrow in this manner include those having the shapes of funnels, drops, or triangles.

In another preferred embodiment, the first and second fluids may be mixed prior to their injection into the mixing chamber (i.e. pre-mixed). For supply channels used to carry out this pre-mixing, the supply channels should be sufficiently long to provide good pre-mixing without being so long as to promote excessive pressure drop. One particular method involves the use of distributing manifolds, so that the streams to be pre-mixed in the supply channels are first divided among a plurality of smaller streams flowing through distribution conduits. These smaller streams of the feed or starting fluids may then be directed at various points, preferably in an arrangement of a repeating or interdigitated sequence, into the supply conduit inlets. By a "repeating sequence" is meant, in the case of two fluids A, B, that fluid streams lie next to one another in a recurring pattern at least one plane. An alternating order of ABAB, for example, is a repeating sequence. Certainly, other repeating sequences are possible, for example AABAAB. Furthermore, the same principals may be used for pre-mixing more than two fluid streams. For example, in the case of three fluids A, B, C, being mixed in a supply channel, the term "repeating sequence" would also encompass many possible orders of individual fluid boundary layers, such as ABCABC or ABACABAC. The fluid layers or distribution conduits from which they are formed may also lie in a repeating sequence in more than one plane. For example, they may be offset in the manner of a chess board in two dimensions. The fluid streams and conduits associated with the different fluids are preferably arranged parallel to one another and in the same direction.

In using a pre-mixing operation as described above to mix two or more streams prior to introduction into the mixing chamber, the fluids to be pre-mixed are divided among a plurality of smaller distribution streams that are then alternately layered or arranged in a repeating sequence before being fed into a supply conduit. Since the supply conduit generally has a significantly smaller cross sectional area than the sum of the cross sectional areas of the individual distribution streams feeding thereto, the pre-mixed stream can be referred to as "focused" prior to introduction into the mixing chamber. This focusing increases the flow velocity of the divided streams and reduces their layer thickness, promoting the formation in the mixing chamber of an inwardly flowing spiral with as many windings as possible.

Preferably, the ratio of the sum of the cross sectional areas of the distribution conduits to the cross sectional area of the supply conduit into which they are merged at its receiving end is from about 1.5 to about 500. When two or more fluids are pre-mixed in this manner, it is preferable that the manifold used for receiving the arranged fluid streams and discharging them into a single conduit (i.e. a supply conduit) have a curved surface where it connects with the supply conduit. To provide optimal mixing characteristics with minimal pressure drop in cases where pre-mixing is used, it is preferred that, with respect to the entire supply conduits, the length to width ratio, assuming a constant cross-sectional geometry, is from about 1 to about 30. Where the supply conduit cross section varies, for example when the supply conduit narrows near the mixing chamber, this ratio applies insofar as it relates to the width of the supply conduit discharge end in fluid communication with the mixing chamber.

As described previously, a fluid spiral is formed that flows concentrically inward, and the resulting mixture is then removed from the center of the fluid vortex. In a specific preferred embodiment where premixing is used, three fluids are mixed, prior to reaction, with the second and third fluids being premixed upstream of the second supply conduit. In this embodiment, the a plurality of second distribution conduits and a plurality of third distribution conduits divide, respectively, the second and third fluids. As explained above, a manifold can be used to receive the second and third fluid distribution conduits arranged in a repeating sequence to force individual boundary layers of the second and third fluid streams in close proximity in the second supply conduit prior to injection into the mixing chamber. The first fluid can be fed into the mixing chamber without mixing through a first supply conduit. This particular embodiment is especially advantageous when the second and third fluids are liquids, injected tangentially, and the first fluid is a gas, injected radially, into the mixing chamber.

The following examples are provided to illustrate certain aspects of the invention, without limiting its broader scope as set forth in the claims.

EXAMPLES 1–5

A static mixer comprising an arrangement of stacked plates and using the principle of cyclone mixing as described previously was constructed of glass to observe cyclone formation under various conditions. Water and air were injected into the mixing chamber in tangential and radial directions, respectively, with respect thereto. A high speed camera with digital image processing was used to observe whether a helical flow of the flowing liquid was established. This was readily determined from observing the path of gas bubbles within the water stream. The results of these experiments are summarized in Table 1.

TABLE 1

| Example # | Water Flow (ml/hr) | Air Flow (ml/hr) | Kinetic Energy Ratio Water/air | Cyclone Formation (Y/N) |
|---|---|---|---|---|
| 1 | 100 | 7,800 | 0.04 | N |
| 2 | 600 | 12,000 | 0.66 | Y |
| 3 | 900 | 12,000 | 1.49 | Y |
| 4 | 600 | 3,600 | 7.41 | Y |
| 5 | 900 | 3,600 | 16.7 | Y |

From these results, the desired spiral flow formation was obtained with a kinetic energy ratio of liquid/gas of 0.66 and higher. The lower bound of the kinetic energy ratio of the tangentially/radially flowing fluids is estimated at about 0.5. It should be noted that much higher throughputs of tangentially flowing fluids may prevent cyclone formation if the flow regime is changed from laminar to turbulent. In this case, however, thorough mixing will still take place.

EXAMPLES 6–7

Experiments were performed using hydrogen peroxide formation conditions described previously. Tests were generally conducted with the reaction mixture of hydrogen and oxygen within the flammability envelope, although the molar ratio of these reactants varied in separate runs. Product hydrogen peroxide was dissolved and measured in a dilute aqueous solution of sulfuric acid and sodium bromide. This solution was passed continuously into the catalytic reaction zone, which was separated from the mixing zone by a conduit. The catalyst used in the reaction zone comprised palladium dispersed on activated carbon. Multilaminar mixing as described previously, using an interdigitated arrangement of fluid streams at the micrometer scale, was used to mix the gaseous reactants thoroughly prior to passing them through the conduit leading to a catalytic reaction zone. The onset of combustion/explosion was easily recognized based on a rapid temperature rise measured along the conduit. Results of this study show that, while combustion occurred with a 500 μm diameter conduit, there was no evidence of combustion when this diameter was reduced to.

EXAMPLES 8–12

Experiments were performed as described above using 80 mg of Pd-containing catalyst on an activated carbon support, a temperature of 83° C., at a constant hydrogen flow of 0.25 normal liters/hr (nl/hr). Again, the catalyst bed was in a reaction zone separated from the upstream multilaminar mixing operation by a conduit, in this case having a diameter of 100 μm. Oxygen flow was increased in a stepwise manner from 0.25 to 5 nl/hr to provide $H_2:O_2$ molar ratios of 1, 0.5, 0.25, 0.125, and 0.05. In each case, a homogeneous reactant mixture was obtained using a method of ultrafast micromixing in accordance with the present invention. While, except for the last experiment, these mixtures were within the flammability envelope, there was no evidence of explosion/combustion. Relative values of hydrogen peroxide yields under each condition are shown in FIG. 1. Despite the fact that most of these tests were performed with hydrogen and oxygen mixtures in explosive concentrations, the mixing/reaction process of the present invention provided a means to generate hydrogen peroxide without the risk of explosion.

EXAMPLES 13–17

Figure 2:
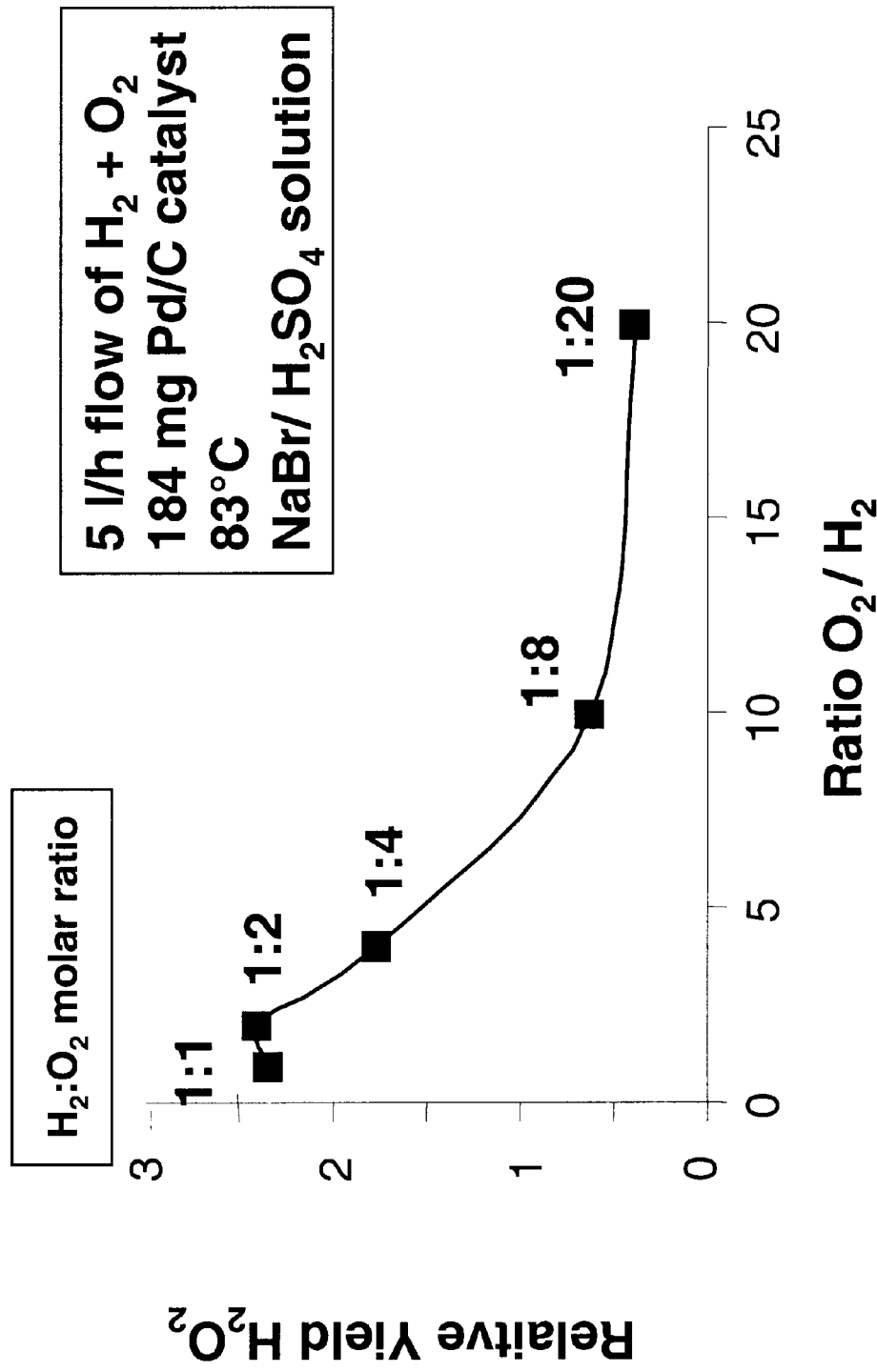
FIG. 2 shows the relationship between hydrogen peroxide product yield and the hydrogen:oxygen molar ratio at a constant total gas flow through the reactor.

Further experiments as described in Examples 8–12 were performed, except that the total flow of hydrogen and oxygen gas was maintained constant at 5 nl/hr. The quantity of catalyst used was 184 mg. Multilaminar micromixing upstream of the reactor again provided a homogeneous mixture of reactants, and no evidence of explosion/combustion was identified. Again, separate tests where hydrogen and oxygen were reacted in molar ratios of 1, 0.5, 0.25, 0.125, and 0.05 were performed. Relative values of hydrogen peroxide yields under these conditions are shown in FIG. 2. These examples further demonstrate the applicability of the process of the present invention to hydrogen peroxide synthesis from the direct reaction of hydrogen and oxygen under a broad range of ratios, both within and outside of the flammability envelope.

What is claimed is:

1. A process for continuously mixing and reacting components existing at least temporarily within their flammability envelope, the process comprising:

a) mixing a feed stream and an oxidant using small scale multilamination mixing to yield a mixed reactant stream having a characteristic mixing time, and;

b) reacting the feed stream and the oxidant, with a characteristic reaction time, in a reaction zone at effective reaction conditions and in the presence of a catalyst to yield an oxidized product, where the ratio of the characteristic mixing time to the characteristic reaction time is less than about 1.

2. The process of claim 1 where the feed stream comprises a species selected from the group consisting of hydrogen, hydrocarbons, and mixtures thereof.

3. The process of claim 1 where the oxidant is oxygen or air.

4. The process of claim 1 where the oxidized product is selected from the group consisting of hydrogen peroxide, ethylene oxide, synthesis gas, and mixture thereof.

5. A process for continuously mixing and reacting a hydrogen containing feed stream and an oxygen containing feed stream, the feed streams existing at least temporarily within their flammability envelope, the process comprising:

a) mixing the feed streams using small scale multilamination mixing to yield a mixed reactant stream having a characteristic mixing time, and;

b) reacting the feed streams, with a characteristic reaction time, in a reaction zone at effective reaction conditions and in the presence of a catalyst to yield a hydrogen peroxide containing product stream, where the ratio of the characteristic mixing time to the characteristic reaction time is less than about 1.

6. The process of claim 5 further comprising, after step (b), reacting the hydrogen peroxide containing product stream with an olefinic product stream selected from the group consisting of a paraffin dehydrogenation process effluent, a methanol-to-olefins process effluent, a thermal cracking process effluent, and mixtures thereof to yield a $C_2$–$C_5$ oxide product.

7. The process of claim 6 where the hydrogen containing feed stream is selected from the group consisting of paraffin dehydrogenation hydrogen effluent stream, a methanol-to-olefins hydrogen effluent stream, a thermal cracking process hydrogen effluent stream, and mixtures thereof.

8. The process of claim 5 further comprising, after step (b), reacting the hydrogen peroxide containing product stream with an intermediate component selected from the group consisting of olefins, ketones, carbonyls, and mixtures thereof to yield a downstream product selected from the group consisting of epoxides, lactones, oximes, and mixtures thereof.

9. The process of claim 8 where the intermediate component is cyclohexanone, the downstream product is cyclohexanone-oxime, and the cyclohexanone-oxime is further reacted to yield caprolactam.

10. The process of claim 5 where the reaction conditions include a temperature from about 20° C. to about 90° C., an absolute pressure from about 1 to about 100 atmospheres, and a gas hourly space velocity from about 50 to about 50,000 $hr^{-1}$.

11. The process of claim 5 where hydrogen is present in the reaction zone in and amount of less than about 3% by volume relative to the amount of both hydrogen and oxygen.

12. The process of claim 5 where the hydrogen containing feed stream and the oxygen containing feed stream are mixed in a proportion such that hydrogen and oxygen are present as an explosive mixture in the reaction zone.

13. The process of claim 12 where the hydrogen to oxygen molar ratio in the reaction zone is from about 0.05 to about 15.

14. The process of claim 5 further comprising, after step (b), passing the mixed reactant stream through a conduit to the reaction zone, where the conduit diameter is less than about 200 μm.

15. The process of claim 5 where the catalyst comprises a support having a noble metal dispersed thereon.

16. The process of claim 15 where the support is selected from the group consisting of inorganic refractory metal oxides, carbon, and polymers.

* * * * *